United States Patent
Frese et al.

(10) Patent No.: US 7,894,071 B2
(45) Date of Patent: Feb. 22, 2011

(54) MEASUREMENT CHIP

(75) Inventors: Ines Frese, Mainz (DE); Elzbieta Nahrstedt, Nieder-Olm (DE); Klaus-Stefan Drese, Mainz (DE)

(73) Assignee: Institut Fuer Mikrotechnik Mainz GmbH, Mainz (DE)

( * ) Notice: Subject to any disclaimer, the term of this patent is extended or adjusted under 35 U.S.C. 154(b) by 264 days.

(21) Appl. No.: 12/086,735

(22) PCT Filed: Dec. 8, 2006

(86) PCT No.: PCT/EP2006/069501

§ 371 (c)(1),
(2), (4) Date: Dec. 12, 2008

(87) PCT Pub. No.: WO2007/074038

PCT Pub. Date: Jul. 5, 2007

(65) Prior Publication Data

US 2009/0161108 A1    Jun. 25, 2009

(30) Foreign Application Priority Data

Dec. 23, 2005   (DE) .................. 10 2005 062 174

(51) Int. Cl.
*G01N 21/00* (2006.01)
(52) U.S. Cl. .................................................. 356/440
(58) Field of Classification Search ............. 356/440, 356/432, 244
See application file for complete search history.

(56) References Cited

U.S. PATENT DOCUMENTS

| | | | |
|---|---|---|---|
| 4,154,233 A | 5/1979 | Brown | |
| 4,273,419 A * | 6/1981 | Geary | 359/615 |
| 5,122,284 A | 6/1992 | Braynin et al. | |
| 5,489,988 A | 2/1996 | Ackley et al. | |
| 5,599,503 A | 2/1997 | Manz et al. | |
| 5,650,123 A * | 7/1997 | Saini et al. | 422/82.11 |
| 5,858,187 A * | 1/1999 | Ramsey et al. | 204/452 |
| 6,100,541 A * | 8/2000 | Nagle et al. | 250/573 |
| 6,316,781 B1 * | 11/2001 | Nagle et al. | 250/573 |
| 6,498,353 B2 * | 12/2002 | Nagle et al. | 250/573 |
| 6,743,581 B1 * | 6/2004 | Vo-Dinh | 435/6 |
| 6,839,140 B1 * | 1/2005 | O'Keefe et al. | 356/436 |
| 6,906,797 B1 * | 6/2005 | Kao et al. | 356/317 |

(Continued)

FOREIGN PATENT DOCUMENTS

DE    19731241    2/1991

(Continued)

*Primary Examiner*—Roy Punnoose
(74) *Attorney, Agent, or Firm*—Michael L. Dunn (57) ABSTRACT

The present invention concerns a measurement chip (1) for carrying out measurements of transmission and/or emission and/or scattering of light by a fluid sample in an operator unit, wherein the measurement chip has a base plate (2) produced from a transparent polymer material, provided in the base plate (2) are at least one measurement cell (3) for receiving a fluid sample and fluid passages (4, 4) for supplying and discharging fluid to and from the measurement cell (3), and provided in and/or on the base plate (2) outside the measurement cell (3) are mirror surfaces (5) which are so arranged that they direct light emitted from and/or scattered by a fluid sample in the measurement cell (3) from the measurement chip (1), preferably in the direction of a light detector provided in an operator unit.

15 Claims, 8 Drawing Sheets

U.S. PATENT DOCUMENTS

| | | | |
|---|---|---|---|
| 7,221,455 B2 * | 5/2007 | Chediak et al. | 356/419 |
| 7,226,562 B2 * | 6/2007 | Holl et al. | 422/68.1 |
| 2003/0235924 A1 | 12/2003 | Adams et al. | |
| 2005/0239210 A1 * | 10/2005 | Iida | 436/164 |
| 2008/0159351 A1 * | 7/2008 | Li et al. | 372/53 |
| 2008/0220414 A1 * | 9/2008 | Jensen et al. | 435/6 |
| 2010/0141951 A1 * | 6/2010 | Ali et al. | 356/436 |

FOREIGN PATENT DOCUMENTS

| | | |
|---|---|---|
| DE | 29622495 U | 2/1997 |
| DE | 19647644 | 5/1998 |
| DE | 10245845 | 4/2004 |
| EP | 1247577 | 10/2002 |
| EP | 1494007 | 1/2005 |
| EP | 1752759 | 2/2007 |
| GB | 2174802 | 11/1986 |
| WO | WO99/44217 | 9/1999 |

* cited by examiner

MEASUREMENT CHIP

BACKGROUND OF THE INVENTION

The invention concerns a measurement chip for carrying out measurements of transmission and/or emission and/or scattering of light by a fluid sample in an operator device and a corresponding measurement system which includes the measurement chip and the operator device. Analytical measurement devices for transmission, emission or scattering measurements on liquid or gaseous samples (fluid samples) are known in the most widely varying design configurations. One use of such measurement devices is that of determining the concentration of an analyte in a fluid sample. For that purpose a fluid sample is introduced into a measurement cell and the concentration of an analyte to be determined is measured on the basis of the absorption or transmission of a coupled-in light beam or on the basis of the emission of light which is delivered by the sample by virtue of fluorescence, luminescence, chemiluminescence or scattering. The absorption or emission of light can be produced or caused by the analyte itself or by another substance which is present in the sample, in dependence on the concentration of the analyte.

Chemical or enzymatic color reactions are frequently used in bio and environmental analysis for determining the concentration of analytes. In dependence on the concentration of the analyte to be investigated, a substrate is chemically or enzymatically converted into a product which has absorption or fluorescence properties which are altered in relation to the initial substrate. Light is coupled into a measurement cell which contains the product and the absorption or transmission of the light which is coupled in or a fluorescence emission caused by the coupled-in light is measured. The measured absorption or transmission or fluorescence is in a direct relationship with the concentration of the analyte to be investigated.

Various methods and devices are used depending on the respective task to be performed. A laboratory standard device is the fluorescence spectrometer which as measurement cells uses cuvettes for receiving fluid samples.

One problem with measurement using conventional fluorescence spectrometers is that only a fraction, about ⅙th, of the emitted fluorescence radiation is measured as light is radiated radially from a sample but the detector is usually arranged only on one side of the sample or the measurement cell. Those spectrometers either have a low level of sensitivity or require photomultipliers which boost the low level of radiation. To overcome the problem of low sensitivity in other known devices many detectors are distributed around the sample or the measurement cell to receive as much emitted radiation as possible. That however is very complicated and expensive.

A further use of analytical measurement devices is position-resolving measurement of fluorescence or angle-dependent measurement of scatter radiation. For example in environmental analysis the proportion of colloid in water samples is determined in accordance with standardised measurement methods on the basis of the angles at which scattering maxima occur or on the basis of the ratios of scatter light intensities with various predetermined scatter angles. Angle-resolving scatter measurements are required for the samples for that purpose. Known devices for angle-dependent fluorescence or scattering measurement use either a large number of detectors which are arranged in fixed measurement angles around the measurement cell, or they use a goniometer in which a detector fixed to a rotating arm is moved over an angular range around the measurement cell. Those apparatuses are highly complicated and expensive in terms of the apparatus involved, costly and take up a great deal of space. They are entirely inappropriate for mobile use.

EP 1 494 007 A1 describes a multi-wave system for fluorescence or absorption measurement, in which deflection of the incident light beam at a mirror ensures that only the light which is given off by the sample or which passes through the sample reaches a detector, but not the incident light. The direction of the incident light is parallel to that of the emitted light. With that apparatus, fluorescence measurement suffers from the disadvantage already described hereinbefore, that only a fraction of the irradiated fluorescence light reaches the detector.

U.S. Pat. No. 4,154,233 describes an apparatus for transmission measurement on fluids using a sample vessel having a V-shaped reflecting bottom. The beam paths of the incident light and the emergent light are parallel. By virtue of reflection at the V-shaped bottom the light passes over a longer distance through the fluid. The apparatus is not suitable for the measurement of light emission or scattering.

EP 1 247 577 A2 discloses a method of detecting whether a liquid or a gas is being passed in a micro-passage system. In that system, a micro-passage is deflected in such a way that two reflection surfaces are produced at the passage walls, which are at an angle of 90° relative to each other. Disposed between the reflection surfaces is a transparent substrate material. If light which is coupled in from a light source impinges on the first reflection surface at an angle of 45°, it is reflected at an angle of 90° to the second reflection surface and is again reflected thereby at an angle of 90° to a detector. The reflection surfaces are totally reflective if the micro-passage is carrying gas so that almost all the light from the light source also arrives at the detector. If the micro-passage is carrying liquid then the surfaces are not totally reflective so that less or no light from the light source reaches the detector. The light arriving at the detector indicates whether the micro-passage is carrying gas or liquid.

U.S. Pat. No. 5,599,503 discloses a miniaturised detector cell in which incident light is reflected a plurality of times within a measurement distance in order even when dealing with small samples to ensure contact which is as long as possible for the incident light with the sample.

DE 102 45 845 discloses a measurement chip having a plurality of pyramid-shaped raised portions in the measurement zone, which serve to increase the surface area and thus to enhance the light intensity for the measurement.

BRIEF SUMMARY OF THE INVENTION

The object of the present invention was that of providing a system for optical concentration and/or particle size determination in fluid samples, which has similar or higher sensitivity than known systems and which at the same time can be produced considerably more easily and less expensively and also using microtechnology.

The object according to the invention is attained by a measurement chip for carrying out measurements of transmission and/or emission and/or scattering of light by a fluid sample in an operator unit, wherein the measurement chip has a base plate produced from a transparent polymer material, provided in the base plate are at least one measurement cell for receiving a fluid sample and fluid passages for supplying and discharging fluid to and from the measurement cell, and provided in and/or on the base plate outside the measurement cell are mirror surfaces which are so arranged that they direct light emitted from and/or scattered by a fluid sample in the measurement cell from the measurement chip, preferably in the direction of a light detector provided in an operator unit.

DETAILED DESCRIPTION OF THE INVENTION

The measurement chip according to the invention is provided as a part or a replacement part of a measurement device which also includes an operator unit for receiving the measurement chip. The operator unit desirably has a space for receiving the measurement chip, in which the measurement chip is either fixedly mounted or into which, and this is particularly preferred, it can be easily interchangeably fitted and removed. An operator unit for use with the measurement chip according to the invention has at least one detector or a plurality of detectors for the detection of light which is coupled out of the measurement chip. The operator unit can further have connections for a fluid connection to the fluid passages of the measurement chip and electronic components for evaluation and/or forwarding of the signals received from the detectors. Chemicals supplies for the chemicals which are not stored on the chip have a fluid actuator means for conveying the fluids. In that way it is also possible to carry out kinetic, continuous and/or also real-time measurement procedures. If the measurement device is to be used for carrying out transmission and/or fluorescence measurement procedures, the operator unit desirably has at least one light source for coupling light into the measurement chip and optionally one or more light filters which allow only predetermined wavelength ranges of the light to pass therethrough. The detectors for the detection of light signals are per se known components which are available on the market. For example CCD chips are suitable. A plurality of detectors and/or position-resolving detectors are provided in the operator unit for certain uses such as for example angle-dependent measurements.

A particular advantage of the measurement chip according to the invention is that the base plate can be produced in the form of a one-piece shaped portion from transparent, moldable material, preferably polymer material, very inexpensively and with a high level of precision by way of shaping methods such as for example injection molding, hot stamping or reaction molding. Preferably shaping methods and materials are so selected that the mirror surfaces are already obtained in the shaping step, without further post-working. Additional metal coatings on the mirror surfaces are possible. The base plate can represent the entire measurement chip, which is quite particularly inexpensive. Or the base plate represents the main part of the measurement chip if separate elements are also to be provided on the base plate, such as for example connecting portions for the fluid passages, further reflecting surfaces (mirror surfaces) in the form of covers or films or fixing or holding elements which are fitted to the base plate after production thereof. In that way the measurement chip can be provided as an inexpensive replacement or disposable part of the measurement device whereas the operator unit which includes the components which are very expensive in comparison with the measurement chip such as for example detectors, light sources, filters, electronic evaluation system and so forth does not have to be replaced. In that way many measurement chips which can only be used once and/or different kinds of measurement chips involving a different structure and for different measurement applications can be used in the same operator unit.

The base plate of the measurement chip according to the invention has at least one measurement cell and at least one fluid passage for the supply of fluid to the measurement cell and at least one fluid passage for the discharge of fluid from the measurement cell. That represents the simplest embodiment of a measurement chip according to the invention, in which respect however many different modifications are possible, which are all embraced by the scope of protection of the invention in accordance with the claims.

In an alternative embodiment the measurement chip according to the invention has a plurality of measurement cells which can be arranged in the base plate in series one after the other in the fluid flow direction, in order for example to determine reaction progresses or reaction kinetics.

In a further alternative embodiment the measurement chip according to the invention has a plurality of measurement cells which are arranged in the base plate in mutually juxtaposed relationship (parallel) with respect to the fluid flow, whereby for example it is possible to implement a plurality of parallel measurement operations. Different fluids can be fed in parallel by way of different fluid passages to a plurality of measurement cells arranged in mutually juxtaposed relationship in the base plate or the same fluid can be fed to each measurement cell in order for example to carry out in parallel transmission, fluorescence or scatter measurement operations using different wavelengths in respect of the excitation light or for different wavelengths of the emitted light (for example using different filters or detectors in the operator units).

In principle a distinction is to be drawn between two kinds of measurement operations, namely measurements of light emission without excitation light, such as for example chemiluminescence measurements, and measurements which require an excitation light such as for example transmission, fluorescence or scatter measurements. The term 'excitation light' is also used in this description in connection with transmission measurements and denotes the light which is coupled in, for the transmission measurement operation.

For measurements of light emissions which require an excitation light, which is the case in the predominant number of measurement methods, in a particularly preferred embodiment of the measurement chip according to the invention further mirror surfaces are provided in the base plate outside the measurement cell, the mirror surfaces being so arranged that they direct into the measurement cell excitation light which is coupled into the measurement chip from a light source arranged outside the measurement chip. That is required for example for transmission, fluorescence and scatter measurement procedures.

In a further preferred embodiment of the measurement chip according to the invention further mirror surfaces are provided in the base plate outside the measurement cell, the mirror surfaces being so arranged that they direct transmission light which passes through the measurement cell and which is coupled into the measurement chip as excitation light from the measurement chip preferably in the direction of a light detector provided in the operator unit. That is required for example for transmission measurements but also for fluorescence and scatter measurements in which transmission is simultaneously determined as a measurement parameter, a checking value or for another purpose.

For applications in which only emission without excitation light is measured, as for example in the case of chemiluminescence measurement operations, the measurement chip according to the invention manages without the aforementioned mirror surfaces for coupling in and coupling out excitation light from a light source arranged outside the measurement chip.

If the measurement chip according to the invention is designed for coupling in excitation light by way of optical mirror surfaces, then the excitation light is introduced into the measurement section in one direction and transmitted light is emitted again on the opposite side of the measurement section. The spatial direction of the measurement cell, in which the excitation light in the aforementioned sense passes through the measurement cell, is referred to in the context of the present description, independently of the dimensions of the measurement cell, as the 'longitudinal axis' of the measurement cell. The greater the dimension of the measurement cell in the direction of its longitudinal axis, the correspondingly more emission radiation or scatter radiation leaves the measurement cell laterally, that is to say radially with respect to its longitudinal axis or radially with respect to the direction of the excitation light introduced. The mirror surfaces according to the invention which are provided in the base plate of the measurement chip for directing the light emitted from and/or scattered by a fluid sample in the measurement cell out of the measurement chip (in contrast to mirror surfaces for directing excitation light which is coupled into the chip and possibly transmitted) direct the light on to one or more light detectors provided in an operator unit. Desirably the detector or detectors is or are arranged in the operator unit beneath or above the measurement section so that a part of the emitted light is incident directly on the detector or detectors. The remaining proportion of the light emitted laterally of the measurement cell or at least a large part thereof is directed by way of the mirror surfaces in and/or on the base plate of the measurement chip on to the detector or detectors. That means that a proportion of the emitted light, which is considerably greater in comparison with many known measurement devices, is detected, whereby the measurement procedures become markedly more sensitive.

In a preferred embodiment of the measurement chip according to the invention the measurement cell is of a rectangular or square cross-section, perpendicularly to its longitudinal axis. In an alternative configuration the measurement cell is of an oval, elliptical or circular cross-section, perpendicularly to its longitudinal axis.

A 'fluid sample' in the sense of the present description and the claims can be a gaseous or liquid sample. A gaseous sample can be for example a pure gas, a gas mixture or an aerosol containing liquid constituents. A liquid sample can be for example a pure liquid substance, a solution, a suspension, a dispersion, an emulsion or a mixture of one of more of the aforementioned.

The term 'mirror surfaces' in the sense of the present description and the claims, even if the term is used in the plural, can also signify a single continuous mirror surface. If for example it is stated that there are provided mirror surfaces which direct transmission light passing through the measurement chip out of the measurement chip in the direction of a light detector in an operator unit, that is then generally and preferably implemented by a single continuous mirror surface arranged in the beam path of the transmission light. Mirror surfaces in the sense of the present invention can be flat surfaces or curved or bent surfaces (convex or concave surfaces). Curved mirror surfaces are desirably used for the deflection or focusing of light which is radiated in different spatial directions on to a detector or another receiver such as for example an optical fiber for passing on the light.

In accordance with the invention mirror surfaces can be produced or provided in different ways. The measurement chip according to the invention can also include different kinds of mirror surfaces. A way of providing mirror surfaces in or on the measurement chip according to the invention, which is particularly preferred in accordance with the invention, is the provision of interfaces at two different media which reflect the impinging light. For that purpose the interface between the polymer material of the base plate of the measurement chip and a gaseous or liquid medium, preferably a gaseous medium and particularly preferably air, is quite particularly preferred. The diffraction angle of the light at such an interface depends on the material-specific refractive index and the angle of incidence of the light. In the case of a truly transparent material as is preferred for the polymer material of the base plate of the measurement chip therefore transmission of the light will become total reflection of the light when the angle of incidence of the light falls below a given angle. The material-specific refractive index of the polymer material will depend on the one hand on the polymer used itself and on the other hand on the surface property or surface roughness. Therefore preferably in accordance with the invention the polymer material, the gaseous or liquid medium and the surface nature of the interfaces which are in the form of mirror surfaces are so selected that the interfaces in the form of mirror surfaces are totally reflecting below a predetermined angle of incidence of the light, preferably at an incidence angle of less than or equal to 45° to the surface or greater than or equal to 45° to the normal to the surface.

The polymer material from which the base plate of the measurement chip according to the invention is produced is preferably acrylate, polymethylacrylate, polymethylmethacrylate, polycarbonate, polystyrene, polyimide, cycloolefin copolymer (COC), cycloolefin polymer (COP), polyurethane, epoxy resin, halogenated acrylate, deuterised polysiloxane, PDMS, fluorinated polyimide, polyetherimide, perfluorocyclobutane, perfluorovinylether copolymer (Teflon AF), perfluorovinylether cyclopolymer (CYTOP), polytetrafluoroethylene (PTFE), fluorinated polyarylether sulfide (FRAESI), inorganic polymer glass and polymethylmethacrylate copolymer (P2ANS). The term 'polymer material' is also used in the sense of the present invention to denote glasses which are suitable for the production of the measurement chip according to the invention.

In a particularly preferred embodiment of the measurement chip according to the invention the mirror surfaces are arranged in the base plate in such a way that light reflected at the mirror surfaces is always reflected back into the polymer material of the base plate. Light which is coupled into the base plate of the measurement chip according to the invention and light which is emitted from the measurement cell by the fluid sample is thus directed to the location where it leaves the base plate for impingement on a detector or a plurality of detectors, exclusively in the polymer material of the base plate and not in the meantime through another medium, except for possible reflection back into the measurement cell. To avoid reflections back into the measurement cell it is possible to also introduce an index matching oil between the light exit and light entrance surfaces of the measurement chip and the operator unit.

The measurement chip according to the invention is suitable not only for carrying out measurements as such on a fluid sample, but in the base plate it can also have passages and spaces for carrying out reactions and/or for mixing fluids. By way of example the measurement chip according to the invention can have a plurality of fluid feed passages for introducing different fluids required for carrying out a chemical, enzymatic or other reaction. In a preferred embodiment according to the invention the measurement chip is designed for implementation of an enzymatic reaction, an antibody reaction or a chemical reaction. For example the measurement chip according to the invention can be designed for carrying out ELISA tests. For that purpose, provided in the base plate is a reaction chamber connected to a plurality of fluid feed passages. A first antibody against an analyte to be determined can be immobilised in the reaction chamber at the wall thereof, or the antibody can be introduced for immobilisation in the reaction chamber through a first fluid feed passage. A sample containing the analyte, washing solutions, a solution containing a second antibody required for the ELISA test and solutions for carrying out a color reaction can be introduced through further fluid feed passages. After implementation of the color reaction in the ELISA test the solution is passed out of the reaction chamber into the measurement cell and therein absorption measurement (transmission measurement) and/or fluorescence or chemiluminescence measurement is carried out.

A further preferred use for the measurement chip according to the invention is carrying out scatter measurements in angle-dependent or angle-independent fashion. Scatter measurements make it possible to determine for example the colloid proportion in a liquid and/or the particle sizes and particle size distributions in a suspension or dispersion. For that purpose reflection of incident light (excitation light) is measured at the particles in a liquid. The scatter angles at which scatter maxima occur or the ratios of the reflected scatter light intensities at different scatter angles in that case provide information about the above-mentioned parameters. For example the proportion of back reflection, that is to say the reflection at an angle of less than 90° to the direction of the incident excitation light, is correspondingly less, the larger the particles in a suspension or dispersion are.

In a particularly preferred embodiment of the measurement chip according to the invention for carrying out angle-dependent scatter measurements (for example for determining clouding and/or for particle size measurement), mirror surfaces are so arranged outside the measurement cell that they deflect light scattered by a fluid sample in the measurement cell in such a way that it leaves the base plate of the measurement chip at various locations and is incident in an operator unit on various light detectors which respectively stand for a scatter angle or scatter angle range, or on various regions of a position-resolving light detector. Individual, mutually separate mirror surfaces can be provided at different angles to the measurement cell for angle-dependent deflection of scattered light out of the measurement chip. Alternatively, it is possible to provide a continuous mirror surface which is so curved that it directs the scattered light in dependence on the scatter angle to the various detectors or to various locations of the position-resolving detector.

Further advantages, features and possible uses of the present invention will be clearly apparent from the description hereinafter of some preferred embodiments and the accompanying Figures.

Figure 1:
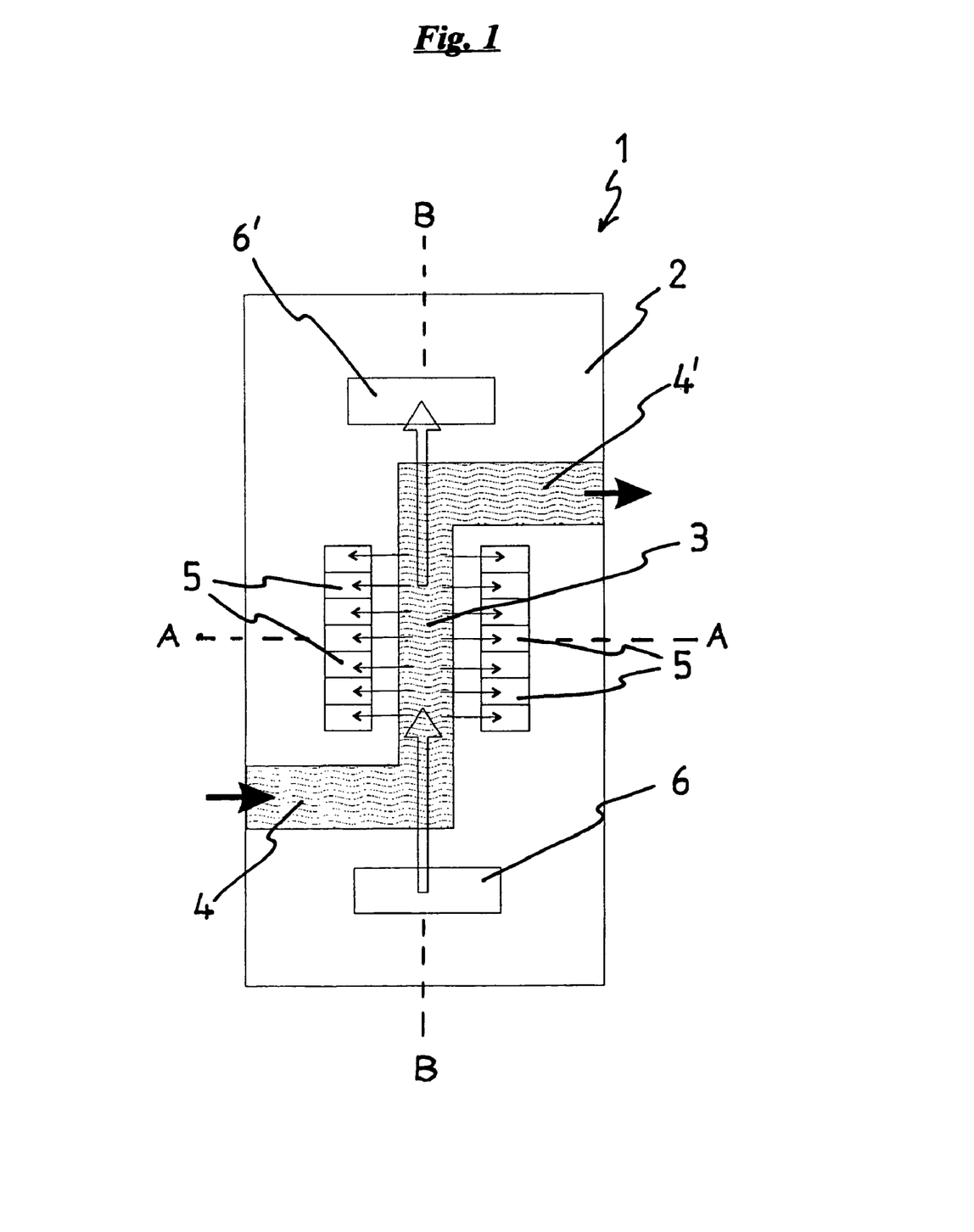
FIG. 1 shows a diagrammatic view of an embodiment of the measurement chip according to the invention from above.

FIG. 1 shows a diagrammatic view of a measurement chip 1 according to the invention from above with a base plate 2 of a transparent polymer material. Fluid passages 4 and 4' for the feed and discharge of fluid are formed in the base plate 2. The fluid flow direction is indicated by black arrows. Disposed between the fluid passages 4, 4' is an elongate measurement cell 3 which, as can be seen from FIG. 2a), is of a substantially square cross-section. The fluid passages 4, 4' meet the longitudinal axis of the measurement cell 3 substantially perpendicularly so that, in a prolongation of the longitudinal axis of the measurement cell 3, there are planar wall surfaces for the introduction of excitation light. In a further prolongation of the longitudinal axis of the measurement cell 3, mirror surfaces 6 and 6' are arranged in the base plate 2, for coupling excitation light in and out. The beam path of the excitation light is shown by open arrows in the Figures. As can be seen from the cross-sectional view of FIG. 2b) excitation light is introduced from a light source 11 provided in an operator unit, into the base plate 3 substantially perpendicularly from below and reflected by the mirror surface 6 and introduced into the measurement cell at an angle of 45° relative to the mirror surface, in the direction of the longitudinal axis of the measurement cell. Transmission light passing through the measurement cell 3 is reflected by the mirror surfaces 6 arranged on the opposite side and directed at an angle of 45° again in the direction of the underside of the base plate 2 so that it is coupled out of the base plate 2 and impinges on a detector 12 in an operator unit.

Provided laterally of the measurement cell 3 in the base plate are further mirror surfaces 5 which direct emission light which is delivered by a fluid sample in the measurement cell and which issues laterally from the measurement cell, in reflection mode to the underside of the base plate 2 where it is coupled out and impinges on a detector 13 in an operator unit.

FIGS. 2a) and 2b) show diagrammatic cross-sections of the measurement chip of FIG. 1 along the lines A-A and B-B respectively. The base plate 2 of the measurement chip 1 comprises transparent polymer material. The mirror surfaces 5 laterally of the measurement cell 3 are shown in FIG. 2a) and the mirror surfaces 6, 6' which are arranged in a prolongation of the longitudinal axis of the measurement cell 3 in the base plate are shown in FIG. 2b). The mirror surfaces 5, 6, 6' are formed by the interfaces between the transparent polymer material and a medium different therefrom, in this case air. For that purpose, provided in the base plate are suitable openings which provide an interface which are at an angle of 45° relative to the exit walls of the measurement cell 3 or the base plate 2. Those interfaces between the polymer material and air are totally reflecting by virtue of the choice of material and the surface nature thereof, below a predetermined angle of light incidence. The light incidence angle at which the interfaces are totally reflecting is at any event less than 45° relative to the mirror surface. The beam path of light which is emitted by a fluid sample in the measurement cell 3 is illustrated by thin arrows by way of example in FIG. 2a).

Figure 2:
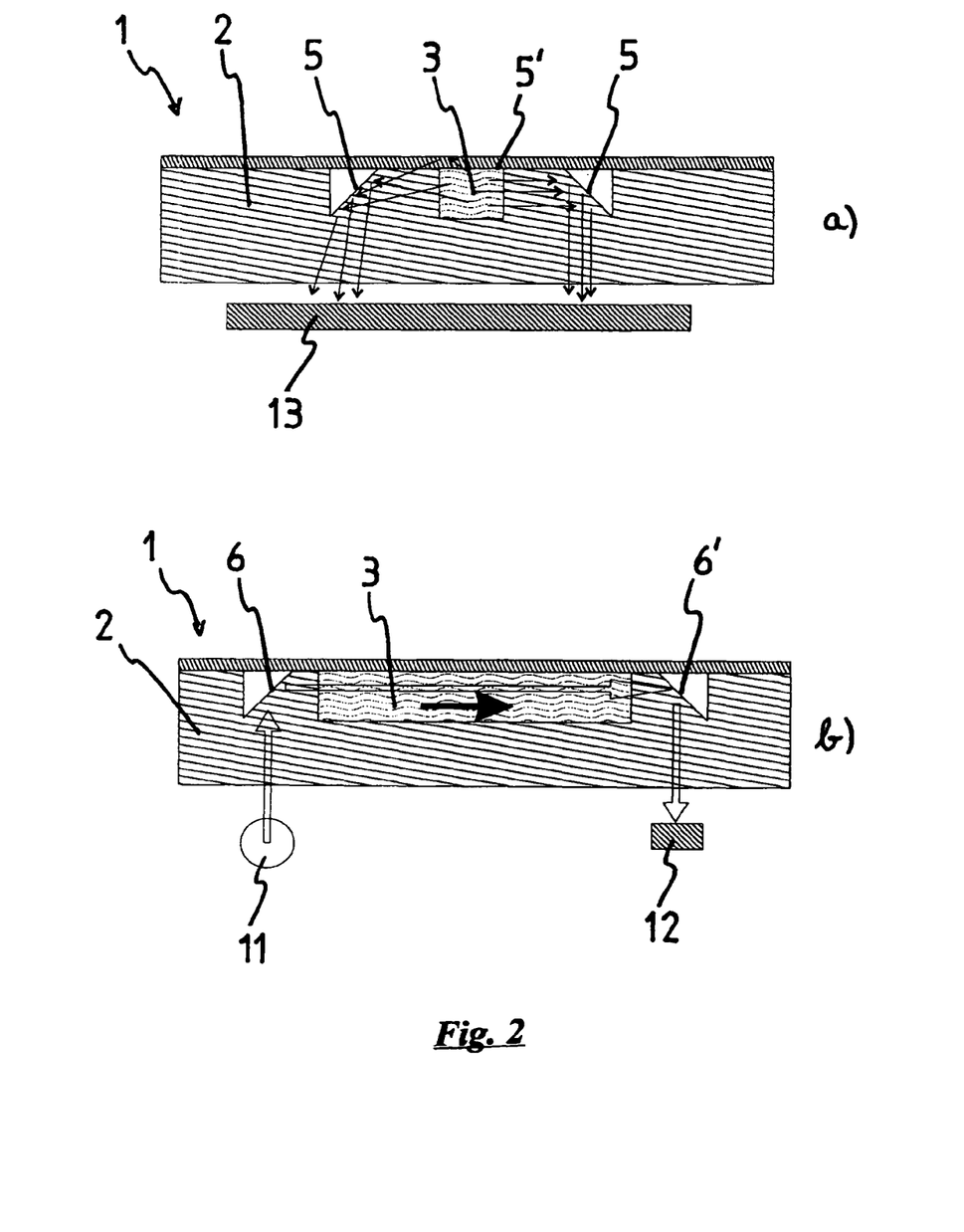
FIG. 2 shows cross-sections through the measurement cell according to the invention of FIG. 1 along lines A-A (FIG. 2*a*) and B-B (FIG. 2*b*)

FIG. 2 shows that a further mirror surface 5' which is not shown in FIG. 1 is provided on the measurement chip on the top side of the base plate. The mirror surface 5' is formed by a reflecting cover film, for example a metal film. Emitted light which does not issue from the fluid sample in the measurement cell 3 laterally out of the measurement cell but upwardly in FIG. 2 is reflected back at the mirror surface 5' afforded by the cover film and either passed directly to the underside of the base plate 3 or passed on to one of the mirror surfaces 5 where it is then further deflected in the direction of the underside of the base plate 3.

FIG. 2a) further shows a diagrammatic view of a detector 13 which is provided in an operator unit and which receives the light which is emitted by a fluid sample in the measurement cell 3 and which is coupled out of the base plate downwardly. In the operator unit, the light received by the detector 13 is evaluated by a suitable electronic system. FIG. 2b) further diagrammatically shows a light source 11 provided in an operator unit for coupling in excitation light and a further detector 12 for receiving transmission light.

The mirror surfaces 5 shown in FIG. 1 are illustrated in the form of a plurality of individual mirror surfaces (seven individual mirror surfaces on each respective side of the measurement cell). That kind of mirror surface arrangement is suitable for example for carrying out a position-resolved fluorescence measurement operation along the measurement section, such as for example for kinetic measurements. The mirror surfaces can be so designed that they direct the emission light issuing from the measurement cell along the longitudinal axis of the measurement cell on to different detectors in an operator unit or on to a position-resolving detector. Alternatively in accordance with FIG. 1 the mirror surfaces 5 on both sides of the measurement cell 3 can be a respective continuous mirror surface so that as much of the emitted light as possible is directed out of the measurement cell 3 with or without position resolution on to a detector.

Figure 3:
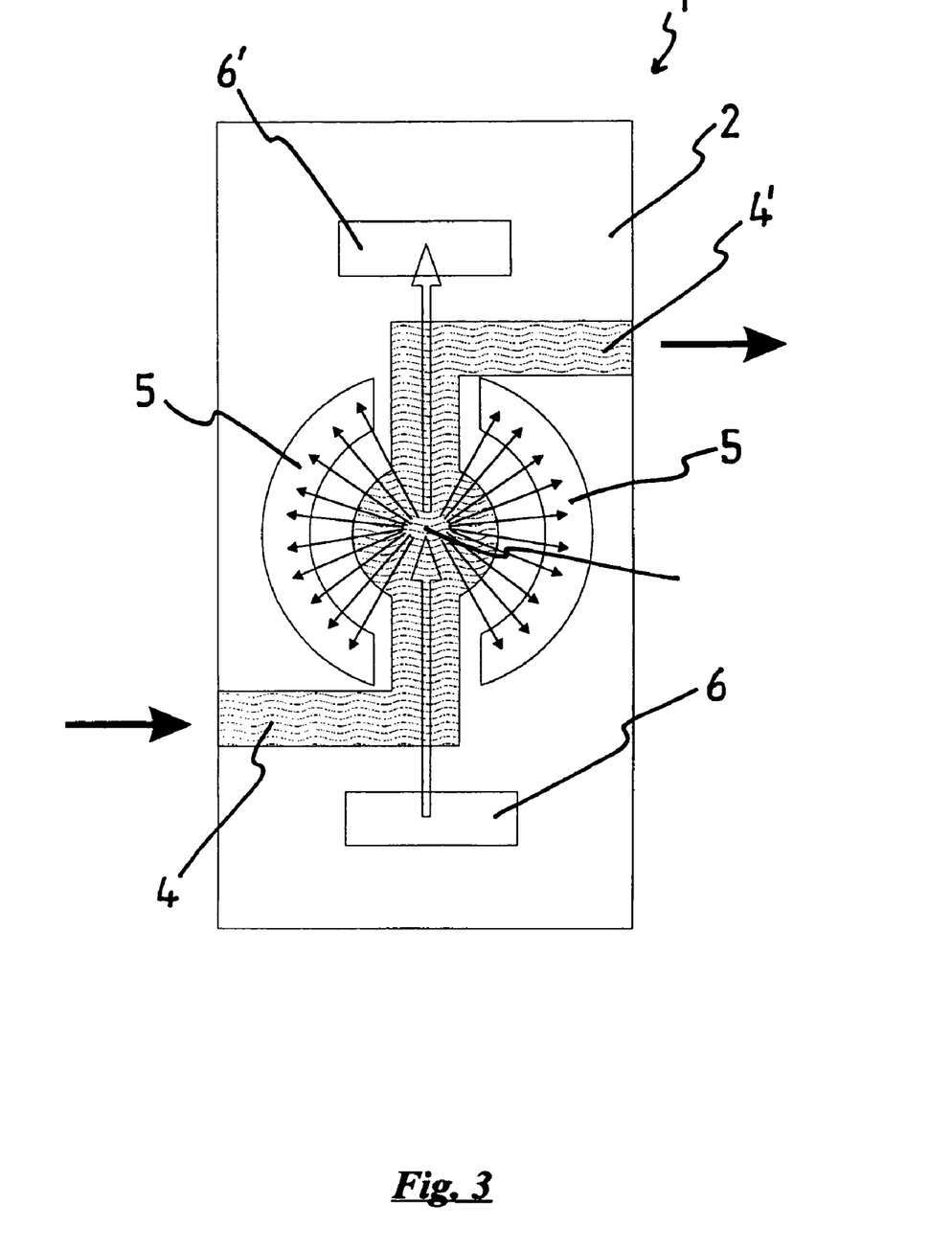
FIGS. 3 through 6 show diagrammatic views of alternative embodiments of the measurement chip according to the invention from above.
Figure 4:
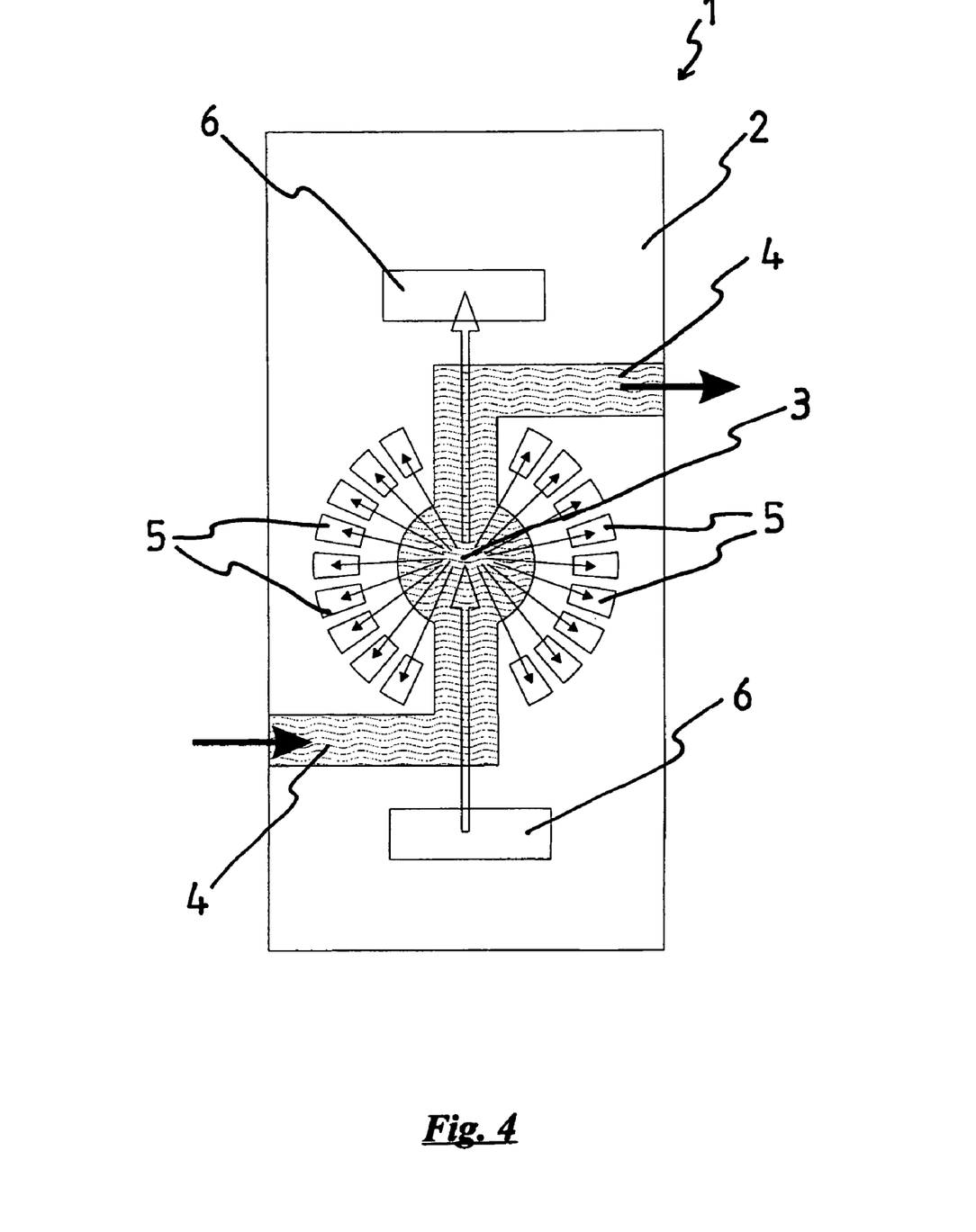

FIG. 3 shows an alternative embodiment of the measurement chip according to the invention which differs from the measurement chip in FIG. 1 substantially in the configuration of the measurement cell 3 and the shape of the mirror surfaces 5. In a plan view the measurement cell 3 is of a substantially circular shape with rounded side surfaces and the mirror surfaces 5 are also shaped in the form of a segment of a circle around the measurement cell 3. The configuration of the measurement cell according to the invention as shown in FIG. 3 is suitable for all kinds of emission measurements and in particular for angle-dependent scatter measurements. The mirror surfaces 5 are continuous mirror surfaces. A plurality of detectors or a position-resolving detector is or are provided in the operator unit for angle-resolving measurement. FIG. 4 shows an embodiment similar to the measurement cell of FIG. 3, wherein the mirror surfaces 5 however are formed by individual, mutually separated mirror surfaces.

Figure 5:
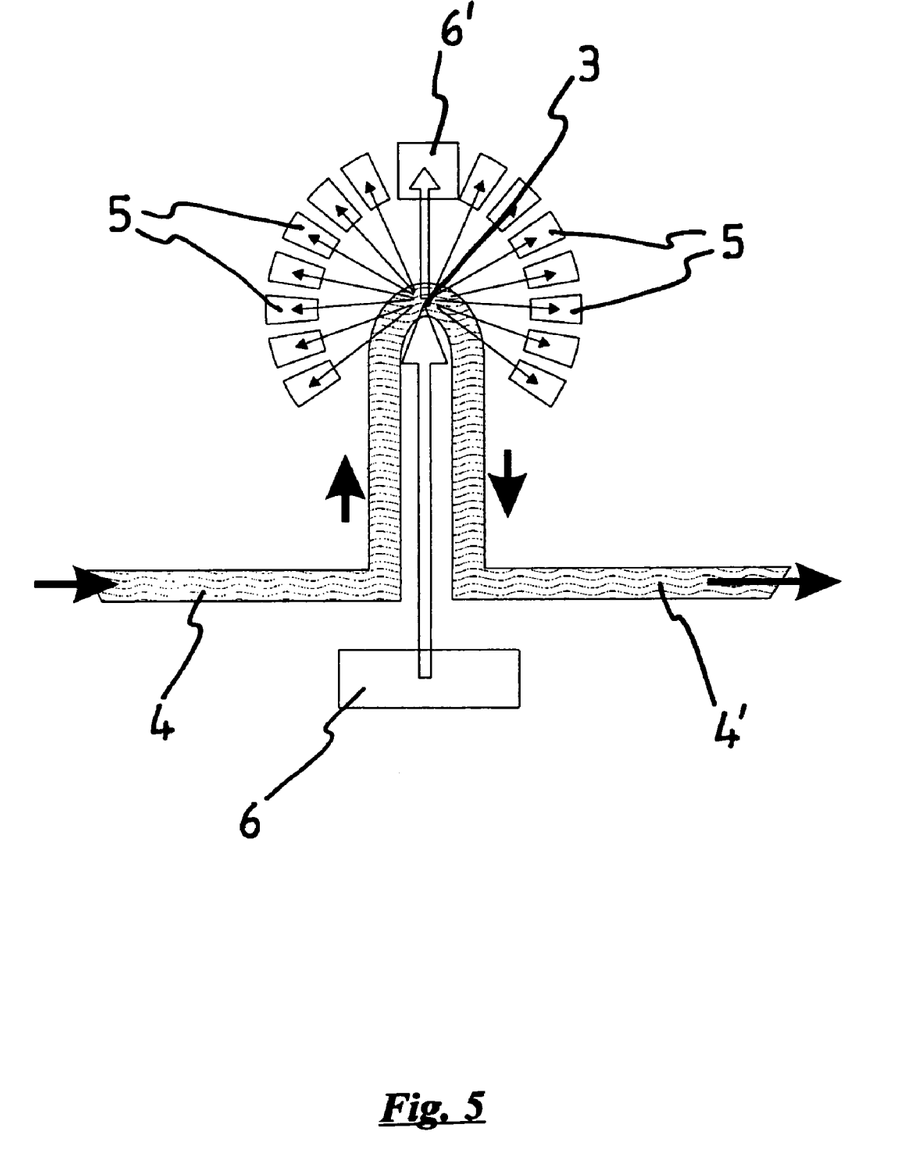

FIG. 5 shows a diagrammatic view of a further alternative embodiment of the measurement chip according to the invention. In this embodiment the fluid passage 4, 4' in the base plate is of a hairpin-shaped configuration and the apex point of the hairpin-shaped configuration forms the measurement cell 3 of the measurement chip. Excitation light is introduced into the region of the measurement cell 3 by way of the mirror surfaces 6 and 6', the light beam impinging laterally on the portion of the fluid passage, that forms the measurement cell. Mirror surfaces 5 for deflection and coupling out emission or scatter light are arranged in the form of a portion of a circle around the portion of the fluid passage, that forms the measurement cell 3. The measurement chip shown in FIG. 5 is suitable for any kind of measurements, in particular for angle-resolving scatter measurements.

Figure 6:
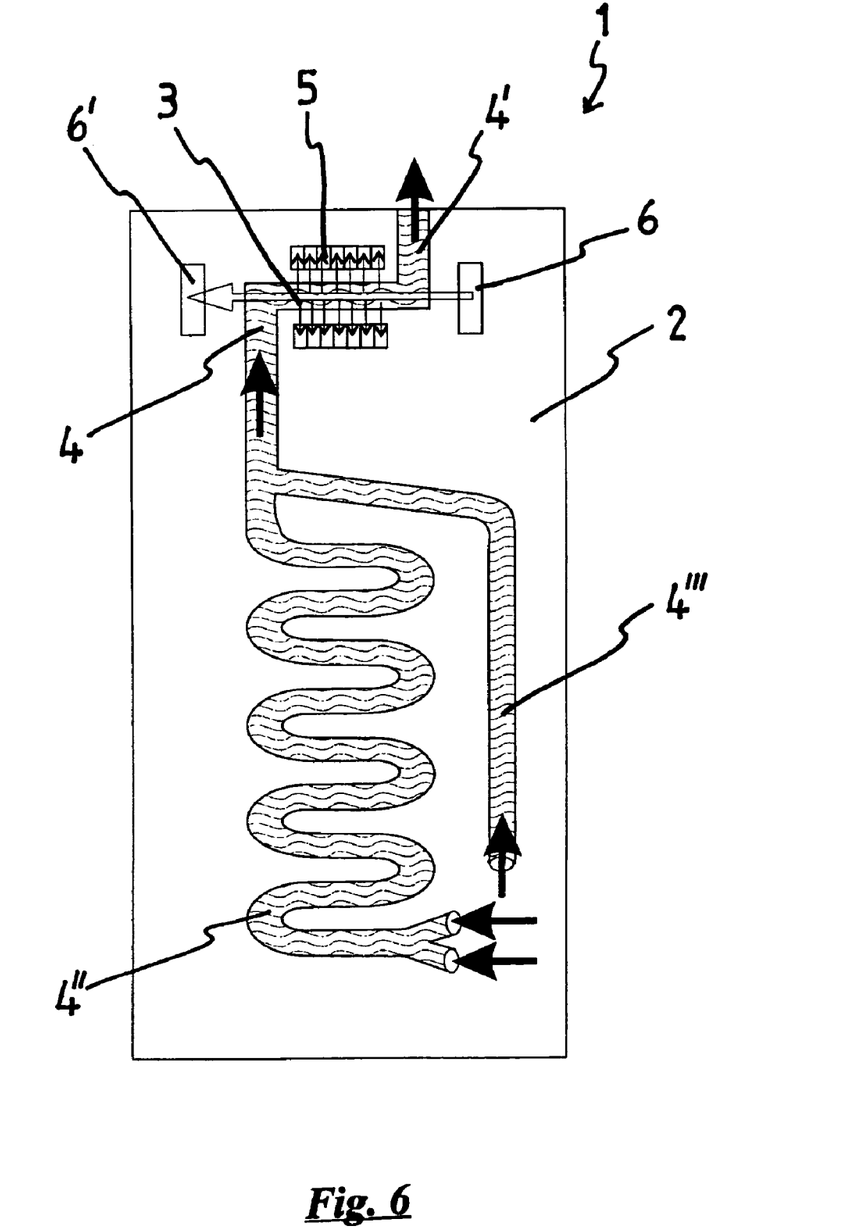

FIG. 6 shows a diagrammatic view of a further embodiment of the measurement chip according to the invention, wherein the region of the base plate which includes the measurement cell 3, the mirror surfaces 6 and 6' for deflection of the excitation light, the mirror surfaces 5 and the fluid passage 4' for the discharge of fluid is formed substantially like the measurement chip shown in FIG. 1. Additionally provided in the base plate are further fluid passages 4" and 4''', wherein the fluid passage 4" has two inlets and is then of a winding configuration in the form of a mixing section and passes with a plurality of changes in direction in the base plate. A further fluid can be meteredly added at the end of the mixing section through a further fluid passage 4'''. This embodiment is only intended to explain by way of example how further elements can be provided in the base plate 2 of the measurement chip 1 according to the invention. The number of fluid passages, the shape thereof and the configuration thereof are to be adapted to the respective demands of reactions, mixing operations or other method steps to be carried out. By way of example it is also possible to provide reaction chambers and further fluid outlets.

Figure 7:
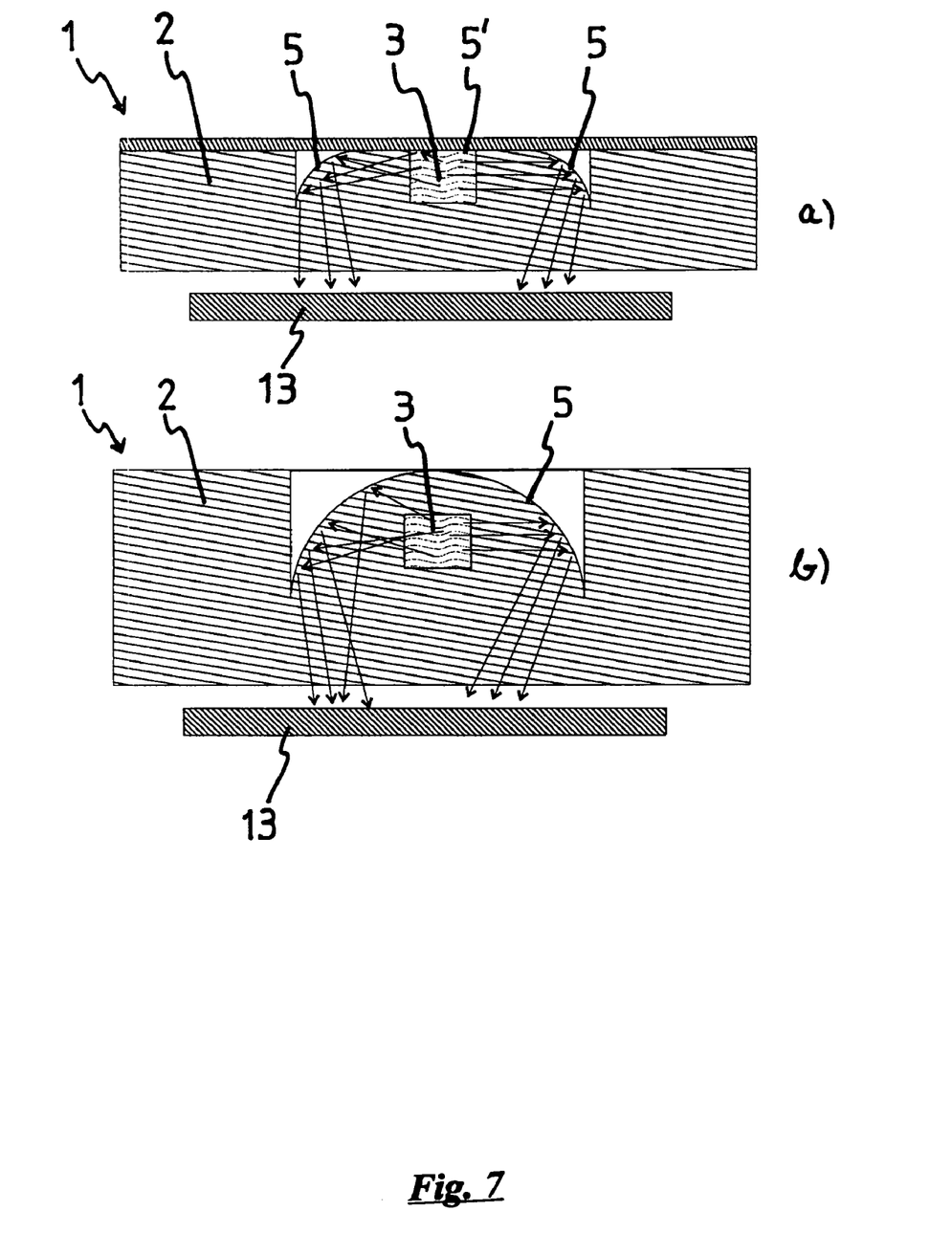
FIG. 7 shows cross-sections through alternative embodiments of measurement chips according to the invention to describe alternative configurations of the mirror surfaces for the deflection of emission or scatter light.

FIG. 7 shows variants of the mirror surfaces according to the invention for the deflection of emission or scatter light. FIG. 7a) shows an embodiment similar to FIG. 2a), wherein however the mirror surfaces 5 are convexly curved for light focusing. FIG. 7b) shows a semicircular convex mirror surface which extends in a semicircular shape around the measurement cell 3 in relation to the bottom surface of the base plate 2 and reflects light which is scattered or emitted from the measurement cell towards the side and upwardly.

Figure 8:
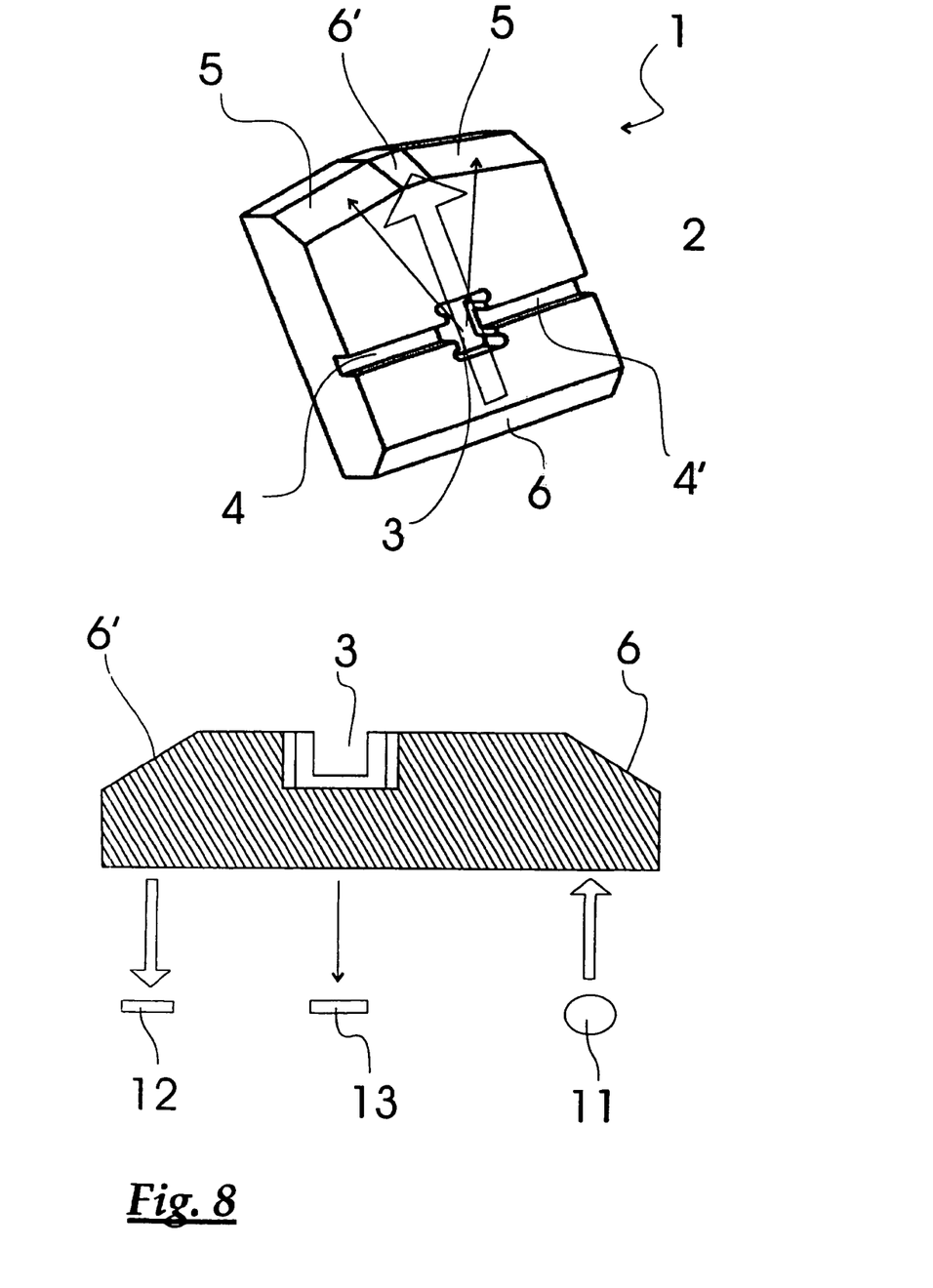
FIG. 8 shows an alternative embodiment of the measurement chip according to the invention for the measurement of angle-dependent scattering at two predetermined scatter angles.

FIG. 8 shows a further alternative embodiment of the measurement chip according to the invention for carrying out angle-dependent scatter measurement as a perspective view from above and in cross-section from the side. Excitation light from a light source 11 in an operator unit is coupled into the base plate 2 of the measurement chip 1 from the underside and deflected in the direction of the measurement cell 3 at a mirror surface 6. Light transmitted through the measurement cell is again deflected on the opposite side of the measurement cell 3 by a mirror surface 6' in the direction of the underside of the base plate 2 and coupled out of the measurement chip. Scatter light issuing from the measurement cell 3 directly in the direction of the underside of the base plate 2 corresponds to a scatter angle of 90° and is there received beneath the base plate 2 by a detector 13 in an operator unit. Light which is scattered by the fluid sample in the measurement cell 3 at a lower scatter angle, in this case a scatter angle of 12°, impinges on the mirror surfaces 5 and is deflected thereby at an angle of 45° in the direction of the underside of the base plate 2, coupled out of the base plate at the underside and received by a corresponding detector (not shown). By way of example the colloid proportion and the particle size distribution in a water sample can be determined from the ratio of the scatter light intensities at the scatter angles of 90° and 12°.

LIST OF REFERENCES 1 measurement chip
2 base plate
3 measurement cell
4, 4' fluid passages
5,5' mirror surfaces (emission, scatter)
6,6' mirror surfaces (transmission)
11 light source (excitation light)
12 detector (transmission light)
13 detector (emission light, scatter light)

What is claimed is:

1. A measurement chip (1) for carrying out measurements of at least one of transmission, emission and scattering of light from a fluid sample in an operator unit, wherein
the measurement chip has a base plate (2) produced from a transparent polymer material,
at least one measurement cell (3) for receiving the fluid sample and fluid passages (4, 4') for supplying and discharging fluid to and from the measurement cell (3) provided in the base plate (2), and the base plate (2) has at least two mirror surfaces (5, 5'), outside the measurement cell (3), which are arranged so that they direct the light from the fluid sample in the measurement cell (3) from the measurement chip in the direction of a light detector (13) provided in an operator unit.

2. A measurement chip as set forth in claim 1 wherein further mirror surfaces (6) are provided in the base plate (2) outside the measurement cell (3), the mirror surfaces being so arranged that they direct into the measurement cell (3) excitation light which is coupled into the measurement chip (1) from a light source (11) arranged outside the measurement chip (1).

3. A measurement chip as set forth in claim 2 wherein further mirror surfaces (6') are provided in the base plate (2) outside the measurement cell (3), the mirror surfaces (6') being so arranged that they direct transmission light which passes through the measurement cell (1) and which is coupled into the measurement chip (1) as excitation light from the measurement chip (1) preferably in the direction of a light detector (12) provided in the operator unit.

4. A measurement chip as set forth in claim 3 wherein at least some of the mirror surfaces are in the form of interfaces between the transparent polymer material of the base plate (2) and a fluid medium and the polymer material, the fluid and the surface nature of the interface mirror surfaces are so selected that the interface mirror surfaces are totally reflecting below a predetermined angle of light incidence.

5. A measurement chip as set forth in claim 3 wherein the mirror surfaces (5, 5', 6, 6') are arranged in such a way that light reflected at the mirror surfaces is always reflected into the polymer material of the base plate (2).

6. A measurement chip as set forth in claim 2 wherein at least some of the mirror surfaces are in the form of interfaces between the transparent polymer material of the base plate (2) and a fluid medium and the polymer material, the fluid and the surface nature of the interface mirror surfaces are so selected that the interface mirror surfaces are totally reflecting below a predetermined angle of light incidence.

7. A measurement chip as set forth in claim 1 where the measurement cell (3) is of a rectangular cross-section in a fluid flow direction.

8. A measurement chip as set forth in claim 1 wherein the base plate (2) is produced from a transparent polymer material selected from the group consisting of acrylate, polymethylacrylate, polymethylmethacrylate, polycarbonate, polystyrene, polyimide, cycloolefin copolymer (COC), cycloolefin polymer (COP), polyurethane, epoxy resin, halogenated acrylate, deuterised polysiloxane, PDMS, fluorinated polyimide, polyetherimide, perfluorocyclobutane, perfluorovinylether copolymer (Teflon AF), perfluorovinylether cyclopolymer (CYTOP), polytetrafluoroethylene (PTFE), fluorinated polyarylether sulfide (FRAESI), inorganic polymer glass and polymethylmethacrylate copolymer (P2ANS).

9. A measurement chip as set forth in claim 1 wherein at least some of the mirror surfaces are in the form of interfaces between the transparent polymer material of the base plate (2) and a fluid medium and the polymer material, the fluid and the surface nature of the interface mirror surfaces are so selected that the interface mirror surfaces are totally reflecting below a predetermined angle of light incidence.

10. The measurement chip of claim 9 wherein the fluid is air.

11. The measurement chip of claim 9 where the angle of light incidence less than or equal to 45° to the surface.

12. A measurement chip as set forth in claim 1 wherein the base plate (2) of the measurement chip (1) has a flat bottom surface.

13. A measurement chip as set forth claim 12 where the mirror surfaces are flat or curved.

14. A device for carrying out measurements of for carrying out measurements of at least one of transmission, emission and scattering of light from a fluid sample where the device includes a measurement chip (1) as set forth in claim 1 and an operator unit, wherein the operator unit has a space for receiving the measurement chip (1) and at least one light source (11) for coupling light into the measurement chip (1) and a detector or a plurality of detectors (12, 13) for the detection of light coupled out of the measurement chip (1).

15. A device as set forth in claim 14 wherein a position-resolving detector (13) is provided in the operator unit for the detection of emission light or scatter light.

* * * * *